Dec. 23, 1958 R. J. POMMERT Plant Pat. 1,782
GLADIOLUS PLANT
Filed April 24, 1958
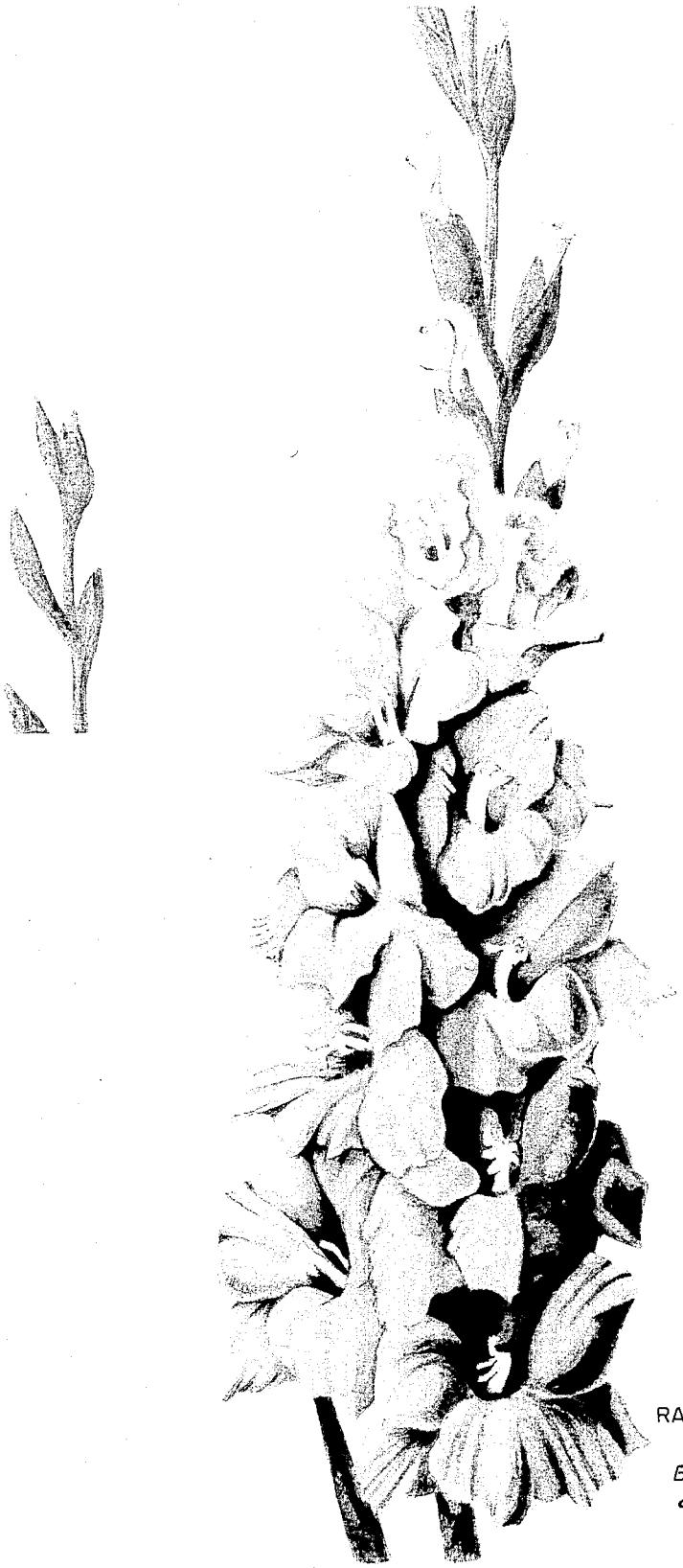
INVENTOR
RALPH J. POMMERT
BY Lamont Johnston
ATTORNEY United States Patent Office Plant Pat. 1,782
Patented Dec. 23, 1958

1,782

GLADIOLUS PLANT

Ralph J. Pommert, Pacific, Wash., assignor to Selected Glads, Inc., Nashville, Tenn., a corporation of Tennessee Application April 24, 1958, Serial No. 730,734

1 Claim. (Cl. 47—60)

My present invention relates to a new and improved variety of gladiolus plant which originated from a cross made by me between the varieties Red Charm (unpatented), as the seed parent, and an unnamed seedling (unpatented) identified as seedling Number 041–16 in my breeding work, as the pollen parent. The new variety originated at my gardens in the State of Washington and I have asexually reproduced the variety at the same location, by natural increase from bulblets. I have observed and tested this new variety through several generations of asexual reproduction and its characteristics appear to be firmly fixed.

This new variety is a very sturdy and vigorous grower, germinates readily, and usually produces good-sized bulbs the first year. The leaf attachment to the stem is loose, making this variety particularly adaptable for cutflower use. This new variety has the ability to open all florets to the tip bud, after the spike has been cut in tight bud and placed in water.

The illustration accompanying this specification shows two views of a single bloom spike of this variety in approximately the true color, but generally reduced in size. The view to the right shows the lower part of the spike and the view to the left shows the upper part.

In the following detailed description, color plate references are to Ridgway's Color Standards and Nomenclature, edition of 1912. Where there are other references to color, the ordinary dictionary meanings of the terms are intended.

The following is a more complete description of the plant and flower of this new variety.

*The plant*

Growth: Sturdy, as compared with the average gladiolus variety. Field-run height of spikes grown under commercial conditions has varied from 50 to 60 inches recorded trials, depending on climate and weather conditions. The average is about 55 inches.

Propagation: Variety germinates easily. Bulblets are average in size, producing good-sized bulbs the first year.

Blooming season: Blooms mid-season. Recorded trials vary from 75 to 90 days, depending upon soil and climate.

Resistance to disease and heat: This new variety has been grown in the typical soils in the Puget Sound area of Washington, under irrigation, and under the natural conditions provided by the climate of the area. At the end of the season, other varieties and the seedlings had succumbed to or been badly affected by various diseases, including Botrytis and Sclerotinia, whereas this variety remained healthy and unaffected. Some thousands of bulbs and bulblets of this variety were grown in commercial field plantings in the vicinity of Lexington, Kentucky, and in the vicinity of Jonesboro, Arkansas, and Oceanside, California, in the year 1957, under climatic conditions normal to these areas, all with results similar to those recorded in the Puget Sound area. It was observed in all these tests that the spike and florets have better than average resistance to the effects of hot sun. Notable, too, is the comparative resistance of this variety to the gladiolus diseases Curvularia and Stemphylium, as indicated by the field tests in the vicinity of Lexington, Kentucky, just mentioned.

Stems: Straight, strong and wiry, being excellent for commercial cutflowers.

Foliage: Upright and medium width, measuring approximately 1¼ inches broad.

Corms: Skin is medium-red and husk is light red.

Spike: Long and wiry, the approximate length being 46 inches when cut for commercial cutflowers, leaving at least 4 full leaves on the plant. Spike rises well above the foliage, with flower heads averaging 23 inches long. Usually, seven florets are fully open at one time, with about 6 buds showing color at this time. Attachment of buds to spike is excellent.

*The flower*

Buds: Arrangement—the buds showing color lie close to the spike, facilitating packing and shipping.

Flower:

*Arrangement.*—The florets are evenly spaced on the spike and all face in the same direction.

*Form.*—Open, somewhat triangular in shape, with slightly waved effect on edges of petals.

*Size.*—Fully opened florets measure 4½ to 5 inches in diameter, without straightening out tips of petals.

*Fragrance.*—None.

*Keeping qualities.*—The spike and florets have better than average resistance to heat. Has excellent opening qualities when cut in the tight bud.

Petals:

*Shape.*—Lightly waved edge, without reflexing of tips. Heavy and slightly raised mid-rib.

*Substance.*—Above average.

*Color.*—In popular terms, the color may be described as a clear scarlet-red, being a slightly brighter shade of scarlet than Scarlet Plate I in Ridgway's Color Standards and Nomenclature. The lower petal is a darker shade of red and is essentially a chromatic self, with a narrow yellow line running thru center of petal from the throat to center.

Reproductive organs: Inconspicuous; about average in length, and of a light shade of red.

I claim:

The new and distinct variety of gladiolus plant, substantially as herein shown and described, characterized particularly by the relative ability of its spike and florets to resist the effects of hot sun, the comparative resistance of the plant to diseases, its straight, strong and wiry stems, the loose attachment of leaves to the stem, the excellent attachment of buds to the spike, lying close thereto, the even spacing of florets on the spike with all facing in the same direction, and the ability to open all florets to the tip bud, after the spike has been cut in tight bud and placed in water.

No references cited.